United States Patent [19]

Braid et al.

[11] Patent Number: 4,474,670

[45] Date of Patent: Oct. 2, 1984

[54] HINDERED PHENYL ESTERS OF CYCLIC BORATES AND LUBRICANTS CONTAINING SAME

[75] Inventors: Milton Braid, Haddonfield; Andrew G. Horodysky, Cherry Hill, both of N.J.

[73] Assignees: Mobil Oil Corporation, New York, N.Y.; Mobil Oil Corporation, New York, N.Y.

[21] Appl. No.: 481,704

[22] Filed: Apr. 4, 1983

[51] Int. Cl.$^3$ .................... C10M 1/54; C10M 5/28
[52] U.S. Cl. .................... 252/32.7 E; 252/33.4; 252/42.7; 252/49.6; 252/51; 252/400 R; 252/401
[58] Field of Search ............. 252/32.7 E, 49.6, 42.7, 252/33.4, 51, 400, 401

[56] References Cited

U.S. PATENT DOCUMENTS

| | | | |
|---|---|---|---|
| 3,254,975 | 6/1966 | Irish et al. | 252/49.6 |
| 3,445,498 | 5/1969 | Cyba | 252/49.6 |
| 3,950,341 | 4/1976 | Okamoto et al. | 252/49.6 |
| 4,162,224 | 7/1979 | Bridger | 252/49.6 |
| 4,328,113 | 5/1982 | Horodysky et al. | 252/49.6 |

*Primary Examiner*—Jacqueline V. Howard
*Attorney, Agent, or Firm*—Alexander J. McKillop; Michael G. Gilman; Claude E. Setliff

[57] ABSTRACT

New reaction products obtained by reacting (1) a hindered phenol, (2) a boron compound and (3) an amine together are described. Preferred reaction sequences are:

(a) (2)+(1), then this product with (3); and
(b) (2)+(3), then this product with (1).

Also described are lubricant compositions containing the reaction products and a method of reducing fuel consumption in an internal combustion engine by lubricating the engine with a lubricant containing the reaction product.

25 Claims, No Drawings

HINDERED PHENYL ESTERS OF CYCLIC BORATES AND LUBRICANTS CONTAINING SAME

BACKGROUND OF THE INVENTION

1. Field of the Invention

The invention is concerned with a novel group of compounds and their use as friction reducing and antioxidant additives in lubricants, i.e. lubricant compositions containing same.

2. Description of the Prior Art

It is known that sliding or rubbing metal or other solid surfaces are subject to wear under conditions of extreme pressure. Wearing is particularly acute in modern engines in which high temperatures and contact pressures are prevalent. Under such conditions, severe erosion of metal surfaces can take place even with present generation lubricants unless a load carrying or antiwear additive is present therein.

Friction is also a problem any time two surfaces are in sliding or rubbing contact. It is of especial significance in an internal combustion engine, because loss of a substantial amount of the theoretical mileage possible from a gallon of fuel is traceable directly to friction.

Borate esters of hindered phenols, i.e. phenols in which both ring positions ortho to the hydroxy group have been substituted by bulky hydrocarbyl groups, are known in the art. U.S. Pat. No. 3,347,793, for example, discloses lubricants containing compounds made by reacting a hindered phenol, e.g., 2,6-di-tert-butyl-p-cresol, with a borate ester. Similarly, U.S. Pat. No. 3,356,707 and U.S. Pat. No. 3,359,298 disclose lubricants containing a product made by reacting a 2,6-tertiary alkyl phenol with a boron compound (e.g., an alkyl borate) to produce a hindered phenol borate ester. The additives are taught to be hydrolytically stable and to possess antioxidant properties. The hindered phenyl borate esters of this invention are believed to be unknown.

SUMMARY OF THE INVENTION

In accordance with this invention, there is provided a reaction product prepared by reacting a hindered phenol, a boron compound and an N,N-di-(2-hydroxyalkyl)-N-hydrocarbyl amine. The invention also provides a lubricant composition comprising a major proportion of lubricant and a minor, antifriction, fuel consumption reducing or antioxidant or high temperature stabilizing amount of said reaction product.

The hindered phenyl borate esters of this invention provide a significant combination of benefits not present in prior art compositions. The additives of this invention combine hydrolytic stability with friction reducing, fuel consumption reducing and oxidative stability properties unattainable using either hindered phenyl borates or alkoxylated amine borates alone. Furthermore, the minor amounts of additive in the lubricant provide a method for hardening lubricated contacting metal surfaces.

DESCRIPTION OF SPECIFIC EMBODIMENTS

The reaction products of this invention, as has been noted, are made by reacting a boron compound, a hindered phenol and an N,N-di-(2-hydroxyalkyl)-N-hydrocarbyl amine to yield a hindered phenyl borate ester. Preferably the reaction to form the product will take place in two stages, the first of which is a reaction of the boron compound with one of the other two reactants to form a product in which at least one of the elements of the boron compound is an ester. The useful boron compounds include boric oxides and compounds of the general structure $$(RO)_p(BO_2)_qY_nZ_r$$

wherein R, Y and Z are hydrogen or alkyl groups containing 1 to 6 carbon atoms, p, n and r are 0 to 2 and q is 1 to 3. Included within the formula are boric acid, metaboric acid, the alkyl metaborates, the alkyl boroxines, boroxine, boroxides and the like.

The hindered phenols that are contemplated have the formula

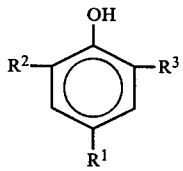

where $R^2$ and $R^3$ are the same or different alkyl group containing 4 to 18 carbon atoms, preferably a tertiary alkyl group. Broadly, the carbon atoms of the alkyl group can be in any isomeric arrangement provided that the carbon atom bonded to the phenyl group is itself bonded to at least two other carbon atoms or chain segments, and $R^1$ is a $C_1$ to $C_{30}$ hydrocarbyl group, i.e., an alkyl, alkenyl, cycloalkyl, aryl, aralkyl or alkaryl group which may have substituted thereon other groups, e.g., an alkoxy group, an alkylthio group or the like.

The hindered phenols include 2,6-di-t butylphenol, 2,6-di-t-butyl-4-butoxyphenol, 2,6-di-t-butyl-4-carbobutoxyphenol and 3,5-t butyl-4-hydroxybenzyl pivalate and the like.

The temperature of reaction of phenol and boron compound can be from about 125° C. to about 250° C., preferably about 140° C. to about 225° C., the precise temperature being selected on the basis of the particular reactants used. A wide range of reactant proportions is contemplated, but will generally and preferably range from a mole ratio of boron containing compound to phenol of from 0.1:1 to about 1:15. The amine to be used in the practice of this invention is one coming within the formula $$R^4N(R^5OH)_2$$

wherein $R^4$ is a hydrocarbyl group (as defined hereinabove) containing 4 to 30 carbon atoms and $R^5$ is an alkylene or substituted alkylene group containing 1 to 12 carbon atoms. These hydroxyamines can be produced by conventional methods through the reaction of alkylamines with hydrocarbyl oxides, such as ethylene oxide, propylene oxide, butylene oxide and the like as well as the substituted members thereof. Useful amines within the stated formula include bis (2-hydroxyethyl) oleylamine, bis (2-hydroxyethyl)cocoamine, bis (2-hydroxyethyl) octadecylamine, bis (2-hydroxyethyl) stearylamine, bis (2-hydroxyethyl) decylamine, bis (2-hydroxyethyl) tallowamine, bis (2-hydroxyethyl) isostearylamine and bis (2-hydroxyethyl) dodecylamine. Mixtures of these can also be used.

The reaction of the amine with the boron-phenol product, if this intermediate is made first, will preferably be carried out at from about 75° C. to about 250° C. using from about 1 mole to about 2 mole per mole of the intermediate.

As has already been stated, the intermediate product must have at least one boron ester group, although diesters and coordinated diesters may also be initially present. Thus, the boron compound can initially be reacted with either the hindered phenol or with the defined amine. A mono hindered phenyl borate can be converted to the additive of this invention by reaction with the amine. The sequence of reactions can be reversed, so that the amine and the boron compound are reacted first, followed by reaction of the resulting borate ester with the hindered phenol reactant. Alternatively, a suitable stoichiometric mixture of the hindered phenol, amine and boron compound can be subjected to suitable reaction conditions to produce the products of this invention.

Thus a variety of methods are available for use in making the additives. As has been noted the reactions can be carried out over a wide range of temperatures, i.e., from about 75° C. to about 250° C. When using methods other than the preferred one (reaction of phenol and boron compound followed by reaction with amine), the same relative proportions of reactants are to be used as already stated.

The reaction product, whether obtained by (1) reacting the hindered phenol with alkyl borate, followed by reaction of the product thus obtained with a hydroxyamine or by (2) reacting amine and borate followed by reaction of hindered phenol, is believed to be

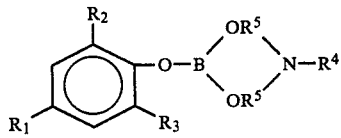

While the reaction product may not consist solely of the structure represented, it is believed that there are substantial quantities of such product present in the subject lubricant and fuel additives.

Of particular significance, in accordance with the present invention, is the ability to improve the fuel use, friction, and oxidation and high temperature stabilizing properties of oleaginous materials such as lubricating media which may comprise either a mineral oil or a synthetic oil or mixtures thereof, or a grease therefrom. In general, mineral oils, both paraffinic, naphthenic oils and mixtures thereof, employed as the lubricating oil or grease vehicle, may be of any suitable lubricating viscosity range. For example, they may range in viscosities of from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800.

In instances where synthetic oils or combinations thereof with mineral oils are preferred, various compounds of this type may be successfully utilized. Typical synthetic vehicles include polyisobutylene, polybutenes, hydrogenated polyolefins, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenol) ether, phenoxy phenylethers. It is to be understood, however, that the compositions contemplated herein can also contain other materials. For example, corrosion inhibitors, extreme pressure agents, viscosity index improvers, co-antioxidants, anti-wear agents and the like can be used, including metal phenates, e.g. calcium or magnesium alkyl phenates, metal sulfonates, e.g. calcium or magnesium aryl sulfonates and zinc phosphorodithioates, i.e. zinc dihydrocarbyl phosphorodithioates. These can be used in amounts in total of from about 0.1% to about 5% by weight, preferably from about 0.5 to about 2% by weight. These materials do not detract from the value of the compositions of this invention, but rather they serve to impart their customary properties to the particular compositions in which they are incorporated. In general, the preformed adducts of the present invention may be employed in any amount which is effective for imparting the desired degree of friction reduction anti-corrosion or anti-wear activity. In many applications, however, the adduct is effectively employed in amounts from about 0.1% to about 10% by weight, and preferable from about 0.5 to about 5% of the total weight of the composition.

With respect to the greases of the invention, a wide variety of thickening agents can be used to prepare them. Included among the useful thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065) calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganicsilicates such as aluminum silicates, magnesium silicates, barium silicates, and the like, containing, in addition to the silicate lattice, varying amount of catio-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15, percent by weight of the total grease composition.

The liquid fuels contemplated include liquid hydrocarbon fuels such as fuel oils, diesel oils and gasolines and alcohol fuels such as methanol and ethanol or mixtures of these fuels. The effective amount of additive therein for fuel use reduction will range from about 5 pounds to about 1,000 pounds thereof per 1000 barrels of fuel, preferably from about 20 pounds to about 50 pounds per 1000 barrels.

The following Examples will present illustrations of the invention. They are illustrative only, and are not meant to limit the invention. Parts are by weight.

EXAMPLE 1

2,6-Di-tert-butyl-4-methylphenyl Borate

A mixture of 2,6-Di-tert-butyl-4-methylphenol (1980 g.), boric acid (93 g.) and xylene (200 ml) was heated while stirring vigorously at 145°–175° C. for 3.5 hours and water (28 ml) was collected by azeotropic stillation. During the next 12 hour three increments of xylene (200 ml each) were periodically added, the temperature was raised to 200° C., and water (63 ml total) was collected. Solvent and unreacted alkylated phenol were removed by reduced pressure distillation, leaving the product, 2,6-Di-tert-butyl-4-methylphenyl borate, a tan solid.

EXAMPLE 2

A mixture of 2,6-di-tert-butyl-4-methylphenyl borate prepared by the method of Example 1 (31.5 g.) and bis(2-hydroxyethyl) oleylamine, Armak Chemicals Ethomeen 0/12, (39.2 g) was heated to a temperature of 138° C. for 2.5 hours. Removal of unreacted amine by distillation to a pot temperature of 100° C. at a pressure of less than 0.1 mm of mercury left the product as a clear brown viscous liquid.

EXAMPLE 3

A mixture of 2,6-di-tert-butyl-4-methylphenyl borate prepared by the method of Example 1 (815.2 g) and bis(2-hydroxyethyl) oleylamine, Armak Chemicals Ethomeen 0/12, (962 g) was heated under a nitrogen atmosphere for 3.5 hours at a temperature of 130°–138° C. while water produced in the reaction was collected as distillate. The reaction mixture was then stripped to a pot temperature of 138° C. at less than 0.1 mm of mercury pressure with only a minor amount of distillate collected. The product was a dark viscous oil.

EVALUATION OF THE COMPOUNDS

The compounds were evaluated in a low velocity friction apparatus (LVFA) in a fully formulated 5W-20 oil containing 20% by weight of an additive package including antioxidant, dispersant and detergent. The friction reducing compound was 1–5% of the total weight of oil. Base oil had the following general characteristics:

| Kinematic Viscosity | @ 100° C. - 6.8 cs |
| --- | --- |
| | @ 40° C. - 36.9 cs |
| Viscosity Index | 143 |

DESCRIPTION

The Low Velocity Friction Apparatus (LVFA) is used to measure the coefficient of friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

Procedure

The rubbing surfaces and 12–13 ml. of test lubricants (5W/20 fully formulated base synthetic oil containing a detergent/dispersant/inhibitor package) are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25–195 rpm), is obtained. A minimum of three measurements is obtained for each test lubricant. Then, the test lubricant and specimens are heated to 250° F., 240 psi, and 40 fpm sliding speed. Afterward, measurements of $U_k$ vs. speed were taken at 240, 300, 400, and 500 psi. Freshly polished steel specimens are used for each run. The surface of the steel specimens are used for each run. The surface of the steel is parallel ground to 4 to 8 microinches. The results in Table 1 refer to percent reduction in friction compared to the unmodified oil. That is, the formulation mentioned above was tested without the compound of this invention and this became the basis for comparison. The results were obtained at 250° F. and 500 psi.

TABLE 1

| | FRICTION CHARACTERISTICS | | |
|---|---|---|---|
| | Additive Conc., | % Reduction in Coefficient of Friction | |
| Composition | Wt. % | 5 Ft./Min. | 30 Ft./Min. |
| Base Oil | 0 | 0[b] | 0[b] |
| Base Oil Plus Example 1 | 4 | 41 | 37 |
| Base Oil Plus Example 2 | 4 | 37 | 33 |

[b]Result for base oil taken as zero.

The products were also evaluated for their oxidative stability. In most cases improvements in oxidative stability over the base oil were observed. Basically the test lubricant (a 150 second paraffinic neutral mineral oil containing the product) is subjected to a stream of air which is bubbled through at the rate of 5 liters per hour at 325° F. for 40 hours. Present in the composition are samples of metals commonly used in engine construction, namely, iron, copper, aluminum and lead. See U.S. Pat. No. 3,682,980, incorporated herein by reference, for further details of the test. Improvement in viscosity index or neutralization number (or both) shows effective control. See the results in Table 2.

TABLE 2

| Additive | Additive Conc., Wt. % | NN | KV, % Increase |
|---|---|---|---|
| Base Oil | 0 | 17 | 334 |
| Di-tert-butyl-p-p-cresol | 1 | 6.2 | 75 |
| | 0.5 | 6.9 | 79 |
| Example 2 | 1 | 4.7 | 69 |
| | 0.5 | 5.2 | 73 |

The hindered phenyl esters of this invention substantially improve the gasoline fuel economy of lubricating oils in engine tests and significantly reduce the observed coefficients of friction when evaluated in bench-scale evaluations. Improvements in energy efficiency are expected in a wide variety of automotive and industrial lubricants containing additive concentrations of these non-metallic, non-phosphorus containing compositions. In addition, they are multifunctional additives which provide significant antioxidation and high temperature stabilizing properties not available in some other friction reducing additives. Other beneficial properties provided by these esters may include substantial antirust, dispersant/detergent, and antifatigue/metal hardening and related antiwear activity.

We claim:

1. A reaction product prepared by reacting (1) a hindered phenol of the formula

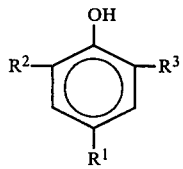

wherein $R^1$ is a $C_1$ to $C_{30}$ hydrocarbyl group and $R^2$ and $R^3$ are the same or different alkyl groups containing 4 to 18 carbon atoms, (2) a boron compound of the formula

$(RO)_p(BO_2)_qY_nZ_r$ wherein R, Y and Z are selected from the group consisting of hydrogen and a $C_1$ to $C_6$ alkyl group, p, n and r are 0 to 2 and q is 1 to 3 and (3) an amine of the formula $R^4N(R^5OH)_2$ wherein $R^4$ is a hydrocarbyl group containing 4 to 30 carbon atoms and $R^5$ is an alkylene or substituted alkylene group containing 1 to 12 carbon atoms, the reaction being carried out at from about 75° C. to about 250° C. and with proportions of reactants to give a phenol:boron compound ratio of from about 0.1:1 to abut 1:15 and from about 1 to about 2 mole equivalents of amine based on each mole of the phenol:boron compound moiety formed.

2. The product of claim 1 wherein said alkyl groups are tertiary alkyl groups.

3. The product of claim 1 wherein said hydrocarbyl groups are selected from the group consisting of alkyl, alkenyl, cycloalkyl, aryl, aralkyl and alkaryl.

4. The product of claim 1 wherein the phenol is 2,6-di-tert-butyl-4-methylphenol, the boron compound is boric acid and the amine is bis(2-hydroxyethyl)oleylamine.

5. A lubricant composition comprising a major amount of a lubricating oil or grease therefrom and an antifriction amount of a reaction product prepared by reacting (1) a hindered phenol of the formula

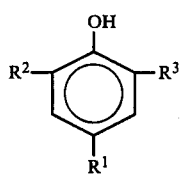

wherein $R^1$ is a $C_1$ to $C_{30}$ hydrocarbyl group and $R^2$ and $R^3$ are the same or different alkyl groups containing 4 to 18 carbon atoms, (2) a boron compound of the formula $(RO)_p(BO_2)_qY_nZ_r$ wherein R, Y and Z are selected from the group consisting of hydrogen and a $C_1$ to $C_6$ alkyl group, p, n and r are 0 to 2 and q is 1 to 3 and (3) an amine of the formula $R^4N(R^5OH)_2$ wherein $R^4$ is a hydrocarbyl group containing 4 to 30 carbon atoms and $R^5$ is an alkylene or substituted alkylene group containing 1 to 12 carbon atoms, the reaction being carried out at from about 75° C. to about 250° C. and with proportions of reactants to give a phenol:boron compound ratio of from about 0.1:1 to abut 1:15 and from about 1 to about 2 mole equivalents of amine based on each mole of the phenol:boron compound moiety formed.

6. The composition of claim 5 wherein said alkyl groups are tertiary alkyl groups.

7. The composition of claim 5 wherein said hydrocarbyl groups are selected from the group consisting of alkyl, alkenyl, cycloalkyl, aryl, aralkyl and alkaryl.

8. The composition of claim 5 wherein the phenol is 2,6-di-tert-butyl-4-methylphenol, the boron compound is boric acid and the amine is bis(2-hydroxyethyl)oleylamine.

9. The composition of claim 5 wherein said lubricant is (1) a mineral lubricating oil, (2) a synthetic lubricating oil or mixtures thereof, (3) mixtures of (1) and (2) and (4) a grease from any of (1), (2) and (3).

10. The composition of claim 9 wherein the lubricating oil is a mineral oil.

11. The composition of claim 9 wherein the lubricating oil is a synthetic oil.

12. The composition of claim 11 wherein the synthetic lubricating oil is a mixture of synthetic oils.

13. The composition of claim 9 wherein the lubricating oil is a mixture of (1) a synthetic oil, or a mixture of synthetic oils and (2) a mineral oil.

14. The composition of claim 9 wherein the lubricant is a grease.

15. A method of reducing fuel consumption in an internal combustion engine which comprises lubricating said engine with a lubricant composition comprising a major amount of a lubricating oil and a fuel consumption reducing amount of a reaction product prepared by reacting (1) a hindered phenol of the formula

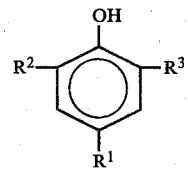

wherein $R^1$ is a $C_1$ to $C_{30}$ hydrocarbyl group and $R^2$ and $R^3$ are the same or different alkyl groups containing 4 to 18 carbon atoms, (2) a boron compound of the formula

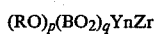
$(RO)_p(BO_2)_qY_nZ_r$ wherein R, Y and Z are selected from the group consisting of hydrogen and a $C_1$ to $C_6$ alkyl group, p, n and r are 0 to 2 and q is 1 to 3 and (3) an amine of the formula

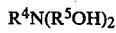
$R^4N(R^5OH)_2$ wherein $R^4$ is a hydrocarbyl group containing 4 to 30 carbon atoms and $R^5$ is an alkylene or substituted alkylene group containing 1 to 12 carbon atoms, the reaction being carried out at from about 75° C. to about 250° C. and with proportions of reactants to give a phenol:boron compound ratio of from about 0.1:1 to abut 1:15 and from about 1 to about 2 mole equivalents of amine based on each mole of the phenol:boron compound moiety formed.

16. The method of claim 15 wherein said alkyl groups are tertiary alkyl groups.

17. The method of claim 15 wherein said hydrocarbyl groups are selected from the group consisting of alkyl, alkenyl, cycloalkyl, aryl, aralkyl and alkaryl.

18. The method of claim 15 wherein the phenol is 2,6-di-tert-butyl-4-methylphenol, the boron compound is boric acid and the amine is bis(2-hydroxyethyl)oleylamine.

19. The method of claim 15 wherein said lubricant is selected from the group consisting of (1) a mineral lubricating oil, (2) a synthetic lubricating oil, mixtures of synthetic oils and (3) mixtures of (1) and (2).

20. A method of hardening lubricated contacting metal surfaces which comprises lubricating said metal surfaces with a lubricant composition comprising a major amount of a lubricating oil or grease therefrom and an antifriction amount of a reaction product prepared by reacting (1) a hindered phenol of the formula

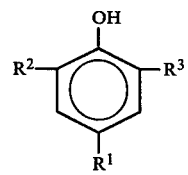

wherein $R^1$ is a $C_1$ to $C_{30}$ hydrocarbyl group and $R^2$ and $R^3$ are the same or different alkyl groups containing 4 to 18 carbon atoms, (2) a boron compound of the formula

$(RO)_p(BO_2)_qY_nZ_r$ wherein R, Y and Z are selected from the group consisting of hydrogen and a $C_1$ to $C_6$ alkyl group, p, n and r are 0 to 2 and q is 1 to 3 and (3) an amine of the formula

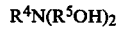
$R^4N(R^5OH)_2$ wherein $R^4$ is a hydrocarbyl group containing 4 to 30 carbon atoms and $R^5$ is an alkylene or substituted alkylene group containing 1 to 12 carbon atoms, the reaction being carried out at from about 75° C. to about 250° C. and with proportions of reactants to give a phenol:boron compound ratio of from about 0.1:1 to abut 1:15 and from about 1 to about 2 mole equivalents of amine based on each mole of the phenol:boron compound moiety formed.

21. The method of claim 20 wherein said alkyl groups are tertiary alkyl groups.

22. The method of claim 20 wherein said hydrocarbyl groups are selected from the group consisting of alkyl, alkenyl, cycloalkyl, aryl, aralkyl and alkaryl.

23. The method of claim 20 wherein the phenol is 2,6-di-tert-butyl-4-methylphenol, the boron compound is boric acid and the amine is bis(2-hydroxyethyl)oleylamine.

24. The method of claim 20 wherein said lubricant is selected from the group consisting of (1) a mineral lubricating oil, (2) a synthetic lubricating oil, mixtures of synthetic oils and (3) mixtures of (1) and (2).

25. The composition of claim 5 containing additionally one or more additives selected from the group consisting of metal sulfonates, metal phenates and zinc phosphorodithioates.

* * * * *